United States Patent [19]

Schaeffer

[11] 4,287,188
[45] * Sep. 1, 1981

[54] PURINE DERIVATIVES

[75] Inventor: Howard J. Schaeffer, Raleigh, N.C.

[73] Assignee: Burroughs Wellcome Co., Research Triangle Park, N.C.

[*] Notice: The portion of the term of this patent subsequent to Apr. 22, 1997, has been disclaimed.

[21] Appl. No.: 920,625

[22] Filed: Jun. 29, 1978

Related U.S. Application Data

[63] Continuation of Ser. No. 771,778, Feb. 24, 1977, abandoned, which is a continuation-in-part of Ser. No. 608,263, Aug. 27, 1975, abandoned, and Ser. No. 662,900, Mar. 1, 1976, Pat. No. 4,199,574, and Ser. No. 718,105, Aug. 27, 1976, abandoned.

[51] Int. Cl.³ .................... A61K 31/52; C07D 473/18
[52] U.S. Cl. .................................... 424/200; 544/244
[58] Field of Search ...................... 544/244; 424/200

[56] References Cited

U.S. PATENT DOCUMENTS 4,199,574  4/1980  Schaeffer ............................ 424/200

FOREIGN PATENT DOCUMENTS 833006  3/1976  Belgium .

OTHER PUBLICATIONS

Baker et al., *J. Pharm. Sci.*, 54, No. 6, (1965), pp. 845–848.
Leonard et al., *Proc. Nat. Acad. Sci.*, (1970), 67(1), pp. 93–98.

*Primary Examiner*—Paul M. Coughlan, Jr.
*Attorney, Agent, or Firm*—Donald Brown

[57] ABSTRACT

9-(2-Hydroxyethoxymethyl) (and related) derivatives of certain 6-, and 2,6-substituted purines have been discovered to have potent anti-viral activities. Novel compounds and their pharamceutically acceptable salts, pharmaceutical formulations containing the compounds of this invention, and the treatment of viral infections with these formulations are all disclosed. 9-(2-Hydroxyethoxymethyl)guanine and 2-amino-9-(2-hydroxyethoxymethyl) adenine are examples of especially active compounds of this invention. Also preferred because of its high oral absorption is the phosphate and especially the monophosphate of 9-(2-hydroxyethoxymethyl)guanine as well as pharmaceutically acceptable salts thereof.

53 Claims, No Drawings

PURINE DERIVATIVES

This is a continuation of U.S. application Ser. No. 771,778 filed Feb. 24, 1977, now abandoned, which was a continuation-in-part of Ser. No. 608,263 filed Aug. 27, 1975, now abandoned, Ser. No. 662,900 filed March 1, 1976 now U.S. Pat. No. 4,199,574, and Ser. No. 718,105 filed August 27, 1976, now abandoned.

This invention relates to substituted purine compounds and their pharamceutically acceptable salts and to methods of preparing them. In particular this invention relates to the 9-(2-hydroxyethoxymethyl) derivatives of purines such as adenine, guanine, thioguanine and 2,6-diaminopurine and the pharmaceutically acceptable salts of these compounds. In 1971, Schaeffer, et al. (J. Med. Chem., 14, 367 (1971)) reported the syntheses of several purine acyclic nucleosides in a study of adenosine deaminase enzyme-substrate interaction. 9-(2-Hydroxyethoxymethyl)adenine in particular was reported and its substrate activity with adenosine deaminase measured.

It has now been discovered that substituted purines of formula (I)

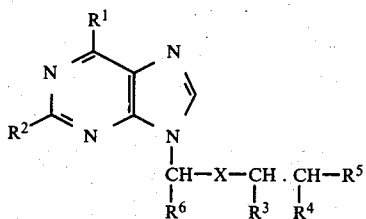

wherein X is oxygen or sulphur and $R^1$, $R^2$, $R^3$, $R^4$, $R^5$ and $R^6$ are various substituents as described herein, have antiviral activity against various classes of DNA and RNA viruses both in in vitro and in vivo experiments. In particular the compounds are active as anti-virals against cytomegalvirus, adenovirus, in particular adenovirus 5, rhino virus, Mengo virus and Sindbis virus. They are especially active as an anti-viral against vaccinia, and herpes viruses, including simplex, zoster and varicella, in mammals, which cause such diseases as for example herpetic keratitis in rabbits and herpetic encephalitis in mice.

According to the present invention there is provided a compound of formula (I) wherein X is sulphur or oxygen, $R^1$ is hydrogen, halogen, hydroxy, alkoxy, azide, thio, alkylthio, amino, alkylamino or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzyloxy, benzoyloxy, benzoyloxymethyl, sulphamoyloxy, phosphate, straight or branched chain or cyclic acyloxy having from 1 to 8 carbon atoms, or substituted carbamoyl group of formula NH.CO—Z wherein Z is alkyl, aryl or aralkyl optionally substituted by one or more of sulphonyl, amino, carbamoyl or halogen; $R^6$ is hydrogen or alkyl, provided that when X is oxygen and $R^2$, $R^3$, $R^4$ and $R^6$ are hydrogen, $R^1$ is not amino or methylamino when $R^5$ is hydrogen or hydroxy, or a salt thereof especially in the form of a pharmaceutically acceptable salt.

Compounds of formula (I), wherein X is sulphur or oxygen; $R^1$ is hydrogen, halogen, hydroxy, alkoxy, azide, thio, alkylthio, amino, alkylamino or dialkylamino; $R^2$ is hydrogen, halogen, amino or azide; $R^3$ is hydrogen, straight or branched chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzoyloxy, benzoyloxymethyl, benzyloxy, sulphamoyloxy, phosphate, carboxypropionyloxy, acetoxy, or substituted carbamoyl group of formula NH.CO—Z wherein Z is alkyl, aryl or aralkyl optionally substituted by one or more of sulphonyl, amino, carbamoyl, halogen; $R^6$ is hydrogen, or alkyl, provided that when X is oxygen and $R^2$, $R^3$, $R^4$ and $R^6$ are hydrogen, $R^1$ is not amino or methylamino when $R^5$ is hydrogen or hydroxy, or a salt thereof, especially in the form of a pharmaceutically acceptable salt are preferred.

Cyclic acyloxy is defined to include alicyclic acyloxy and aromatic acyloxy, i.e. aroyloxy such as benzoyloxy.

Especially preferred are compounds of formula (I) as defined above wherein $R^5$ is straight or branched chain acyloxy containing 1 to 5 carbon atoms, e.g. formyloxy, acetyloxy, propionyloxy, and pivaloyloxy, or an aroyloxy, e.g. benzoyloxy, and most especially wherein $R^1$ is amino or hydroxy, $R^2$ is amino, and $R^3$, $R^4$, and $R^6$ are hydrogen, and their salts, especially their pharmaceutically acceptable salts.

Also especially preferred are compounds of formula (I) as defined above wherein $R^5$ is carboxyacyloxy containing 4 to 6 carbon atoms, e.g. carboxypropionyloxy (i.e. 3-carboxypropionyloxy), carboxybutyryloxy (i.e. 4-carboxybutyryloxy) and carboxyvaleryloxy (i.e. 5-carboxyvaleryloxy), and most especially wherein $R^1$ is amino or hydroxy, $R^2$ is amino, and $R^3$, $R^4$, and $R^6$ are hydrogen and most preferred wherein $R^1$ is hydroxy, $R^2$ is amino, and $R^3$, $R^4$, and $R^6$ are hydrogen, and their salts, especially their pharmaceutically acceptable salts.

For oral administration because of its extremely high absorption when administered orally the monophosphate of 9-(2-hydroxyethoxymethyl)guanine, particularly as a pharmaceutically acceptable salt, is preferred. 9-(2-Hydroxyethoxymethyl)guanine monophosphate has the structure of formula (IA):

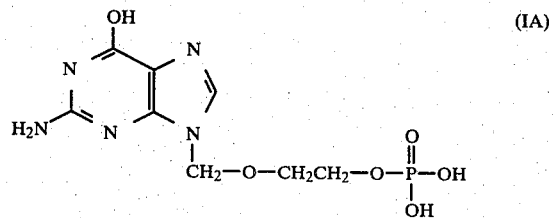

Suitable cations for forming the pharmaceutically acceptable salt include ammonium, sodium, potassium, calcium, magnesium and aluminum cations, among others.

The monophosphate salt is the most preferred and has the structure of formula (IB):

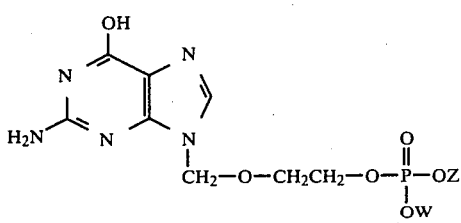

wherein W is selected from hydrogen, sodium, potassium, ammonium, calcium/2, magnesium/2, and aluminum/3 and Z is selected from sodium, potassium, ammonium, calcium/2, magnesium/2, and aluminum/3, most preferably W is hydrogen and Z is sodium or ammonium.

The componds of formulas (IA) and (IB) are administered orally or parenterally at dose levels, calculated as the free phosphate (i.e. formula IA) form, of about 0.1 to 250 mg per kg, preferably 1.0 to 50 mg per kg, of mammal body weight, and are used in a man in a unit dosage form, administered, e.g. a few times daily, in the amount of 1 to 250 mg per unit dose.

The compounds of formulas (IA) and (IB), for parenteral administration or administration topically as drops, e.g. for eye infections, may be presented in aqueous solutions at a concentration of from about 0.1 to 10%, preferably 0.1 to 7%, most preferably 0.2 to 5% w/v.

Alternatively, for infections of the eye or other external tissue, e.g. mouth and skin, ointment or cream topical formulations are preferred. Concentrations of from about 0.1 to 10%, preferably 0.1 to 7%, most preferably 1% may be used.

Pharmaceutical compositions containing a compound of formula (IA) or (IB) may also be used in suppository form.

These pharmaceutical formulations containing a compound of formula (IA) or (IB) are useful for treating mammals having viral infections caused by herpes viruses, including cytomegalovirus, simplex, zoster and varicella, which cause such diseases as for example herpetic keratitis in rabbits and zoster and varicella, which cause such diseases as for example herpetic keratitis in rabbits and herpetic encephalitis in mice.

In the definition of W and Z in formula (IB) the polyvalent cations included are defined as calcium/2, magnesium/2 and aluminum/3 which is intended to mean that cation divided by its valence, i.e. $Ca^{++}/2$, $Mg^{++}/2$ and $Al^{+++}/3$. This is meant to indicate that calcium or magnesium cations are in ionic association with two phosphate oxygens and aluminum with three.

Compounds of formula (I) as defined above wherein X is oxygen; $R^1$ is hydrogen, halogen, hydroxy, alkoxy, thio, alkylthio, amino, alkylamino, dialkylamino or azide; $R^2$ is hydrogen, halogen, amino or azide; $R^3$ is hydrogen, straight or branched chain or cyclic alkyl, hydroxyalkyl or phenyl; $R^4$ is hydrogen, or hydroxy; $R^5$ is hydrogen, hydroxy, benzoyloxy, hydroxyalkyl, amino, carboxypropionyloxy, acetoxy, benzyloxy, benzoyloxymethyl, phosphate, sulphamoyloxy, substituted carbamoyl group of formula NH.CO—Z where Z is alkyl, aryl or aralkyl optionally substituted by one or more of sulphonyl, amino, carbamoyl, halogen; $R^6$ is hydrogen, or alkyl, provided that $R^5$ is hydroxy only when $R^1$ is amino, hydroxy, alkylamino, alkylthio, or dialkylamino, and $R^2$ is amino and $R^6$ is hydrogen; $R^5$ is alkyl-hydroxy only when $R^1$ is hydroxy; $R^5$ is hydrogen only when $R^1$ is hydroxy or halo; when $R^5$ is benzoyloxy $R^2$ is not halogen; $R^5$ is acetoxy only when $R^1$ is hydroxy or amino and $R^2$ is amino or both $R^1$ and $R^2$ a halogen; $R^5$ is a substituted carbamoyl of formula NH.CO—Z wherein Z is a group $CH(NH_2)CH_2C_6H_5$ only when $R^1$ is dialkylamino; except that when $R^5$ is hydroxy and $R^1$ is alkylamino then $R^2$ is not hydrogen; or a salt thereof, especially in the form of a pharmaceutically acceptable salt are particularly preferred.

In particular compounds of formula (I), as hereinbefore defined, where X is oxygen, $R^1$ is halogen, amino, hydroxy or alkylthio; $R^2$ is amino; $R^5$ is hydroxy, benzoyloxy, carboxypropionyloxy, acetoxy or hydroxyalkyl and $R^3$, $R^4$ and $R^6$ are hydrogen, provided that $R^5$ is hydroxyalkyl only when $R^1$ is hydroxy and $R^5$ is acetoxy only when $R^1$ is hydroxy or amino, are most preferred and have been found to be highly active. Compounds where X is sulphur, $R^1$ is halogen, amino or alkylamino and $R^2$, $R^3$, $R^4$, $R^5$ and $R^6$ are hydrogen have also been found to be highly active.

Additionally, the compound where X is oxygen, $R^1$ is hydroxy, $R^2$ is amino, $R^3$, $R^4$ and $R^6$ are hydrogen and $R^5$ is a formyloxy group has been found to be highly active.

The preferred halogen substituent is chlorine. As used herein and throughout the specification the term alkyl is denoted to mean 1 to 12 carbon atoms, preferably 1 to 8 carbon atoms.

Salts which are especially convenient for therapeutic use are salts of pharmaceutically acceptable organic acids such as lactic, acetic, malic, or p-toluenesulfonic acid as well as salts of pharmaceutically acceptable mineral acids such as hydrochloric or sulfuric acid.

In a second aspect of the present invention there is provided a method of preparing a substituted purine of formula (I) or an acid addition salt thereof

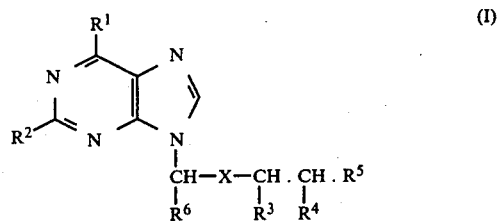

wherein X, $R^1$, $R^2$, $R^3$, $R^4$, $R^5$ and $R^6$ are hereinbefore defined provided that when X is oxygen and $R^2$, $R^3$, $R^4$ and $R^6$ are hydrogen, $R^1$ is not amino or methylamino when $R^5$ is hydrogen or hydroxy; or a salt thereof, especially a pharmaceutically acceptable salt thereof characterised in that:

(a) where in the compound of formula (I) $R^5$ is amino or hydroxy, a protective group Y is replaced in a compound of formula (II) by an amino or a hydroxy group;

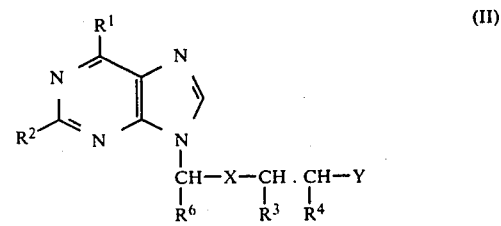

(b) a compound of formula (III) wherein M and G are precursors of groups $R^1$ and $RHU\ 2$ respectively is converted

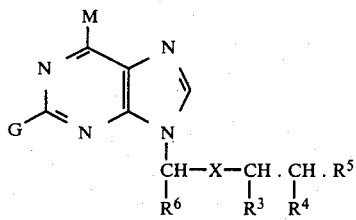

into a compound of formula (I) where $R^1$ and $R^2$, have the values as defined above;

(c) a compound of formula (IV)

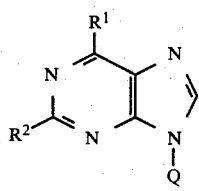

is reacted with a compound of formula (V)

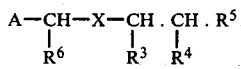

wherein A is a leaving group and Q is an hydrogen atom or a leaving group;

(d) a ring is closed in a precursor compound having either the pyrimidine or imidazole ring incompletely formed;

(e) a blocking group is removed from a compound of formulation (I) wherein one or both of $R^1$ and $R^2$ is blocked; and where the product of said reaction is a base, optionally converting a compound of formula (I) into an acid addition salt thereof, or where the product is a salt of a compound of formula (I), optionally converting said salt into its base or another salt thereof.

In the case of method (a) the 9-ether chain is blocked terminally by a protective group Y which may be an ester, eg an acyloxy group, an amide, eg a phthalimido group, or an arylmethoxy group, eg benzyloxy. In the first instance the acyl group may be aliphatic eg acetyl, or aromatic eg benzoyl, both types of acyl group being removed by mild basic hydrolysis. In general warming with aqueous methylamine will suffice to bring about the deblocking.

Arylmethoxy blocking groups, such as benzyloxy, are removed by hydrogenolysis, either catalytically, as by hydrogen and Raney nickel or palladium-on-charcoal, or chemically, as by sodium in liquid ammonia. When sodium in liquid ammonia is used, an excess of ammonia serves as solvent. For catalytic hydrogenolysis an alkanol is the preferred solvent, although a number of inert, eg non halogen and non-sulphide or mercapto containing solvents may be used provided they dissolve the acyl blocked substrate, eg such solvents as benzene, tetrahydrofuran or dioxane.

Conversion of a compound of formula (III)

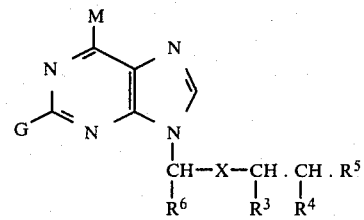

into a compound of formula (I), by method (b), can be achieved in numerous different ways. For example one or both of G and M can be converted into a halogen atom by halogenation; into an hydroxy group by hydrolysis; into a thio or alkylthio group by sulphuration; into an hydrogen atom by reduction or desulphuration; or by formation of the azide. All such methods are well known and can be found in "Heterocyclic compounds—Fused by Pyrimidines Part II Purines Ed. by D. J. Brown (1971) published Wiley-Interscience".

Alternatively conversion can be brought about by using enzymes, for example adenosine deaminase efficiently converts a 2,6 diamino compound to guanine $R^1=OH\ R^2=NH_2$, in an aqueous suspension at about 37° C. and initial pH of about 7.0.

Those compounds that contain precursors of groups $R^1$ and $R^2$ and can be converted into compounds of formula (I) can be considered as intermediates in the synthesis of those compounds.

The intermediate of formula (IX)

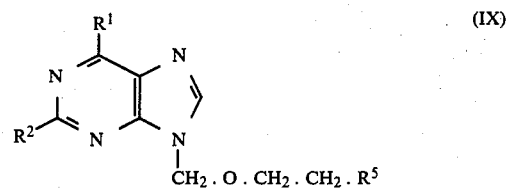

wherein $R^1$ is a hydroxy or amino group, $R^2$ is a hydrogen or halogen atom, or hydrazino group, and $R^5$ is a hydroxy or phthalimido group; and of formula (X)

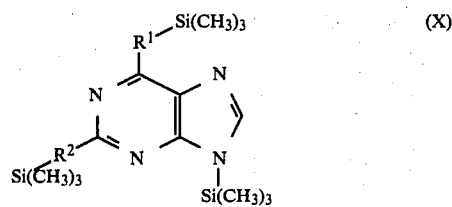

wherein $R^1$ is an NH group and $R^2$ is an NH group, are novel compounds and are therefore provided in a further aspect of the invention.

In method (c) the leaving group A is a reactive residue of an organic or inorganic acid, and may therefore be a halogen atom, or a carboxylate group, and Q is a hydrogen atom or an acyl group. The preferred method comprising the condensation of a purine having the desired 2- and 6-substitution with an acyl or aralkyl-blocked 2-haloalkoxyethanol for instance 2-benzoyloxyethoxymethyl chloride, in a strong polar solvent such as DMF (dimethylsulphoxide) or hexamethylphosphoramide, and in the presence of a base such as triethylamine or potassium carbonate. The reaction is preferably carrier out at room temperature over an extended period of time ie several days may be required to give reasonable yields.

Alternatively a thermal condensation, eg fusion reaction, may be carried out to give the product directly. For this reaction a suitably substituted purine is heated together with an acyloxy-alkoxymethyl carboxylate eg 2-oxa-1-4-butanediol diacetate, in the presence of a catalytic amount of strong acid such as sulphuric acid. Temperatures in excess of 100° C. are generally required, but they should preferably not be greater than about 200° C. in order to minimise decomposition. The temperature should be selected such that the mixture of reactants fuse before they undergo decomposition.

The fusion reaction may also be carried out under substantially the same condition as above, with perhaps somewhat lower temperatures, between a 9-acylpurine and the alkoxmethyl carboxylate or halide. Alternatively the fusion reaction can be carried out using the diester, for instance 2-acetoxyethoxymethyl acetate.

Method (d) involves the ring closure of either the imidazole or pyrimidine ring to give the final product. In the case of the imidazole ring this may be achieved by reaction of the suitably substituted precursor with a one carbon reagent, such as triethylorthoformate, under for example mildly acidic conditions, at a temperature of about 25° C. and for several hours. A suitable precursor is a substituted pyrimidine of formula (VI)

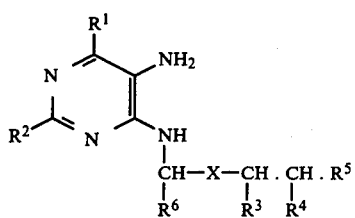
(VI)

An alternative reagent to use is diethoxymethyl acetate, when neutral conditions at about 100° C. for about 10–15 minutes are preferred.

The ring closure of the pyrimidine ring is similar to that for the imidazole ring except that the carbon reagent being added is generally substituted, for example by amino. The blocked, substituted carbon is first attached to the 2-amino group on a precursor of formula (VII)

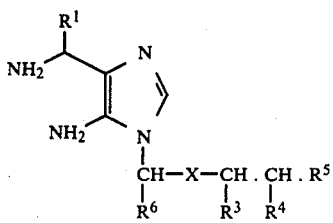
(VII)

and then deblocked and cyclized. Cyclization may be achieved in some cases by treatment with acid, however this should be done as close to neutral as possible. In other cases a compound of formula (VII) can be closed by reaction with one of the standard one carbon reagents, under mild conditions. (See J. Org. Chem 81 (1959) p. 6021 A. Yamazaki et al). It is important in this method that the substitution at the 2 position, ie $R^2$ of formula I, is introduced during ring closure. Suitable substituents in the 6 position, ie $R^1$, are limited, to such groups as thio, amino or hydroxy.

In method (e) substituents $R^1$ and $R^2$ may be blocked by for instance trimethylsilyl groups. Such a compound will be the product of the condensation of a trimethylsilylated purine and an ester or diester as in method (c). Such blocking groups are very labile and can be removed by solvolysis with alcoholic or aqueous ammonia, or by alcoholysis.

Alternatively the mercuric chloride salt of a purine can be prepared in the presence of alkali and then condensed with a haloether in solvent of the aromatic organic type. Prior to preparation of the salt however all reactive substituents on the purine must be blocked, and therefore the last step in this method is the unblocking of the blocked substituents.

In another method, which combines methods (a) and (b) solvolytic deblocking may be effected at the same time as replacement of a purine ring leaving group e.g. halogen, such as by the reaction with liquid ammonia. In this case the leaving group or the purine nucleus is replaced by an amino group at the same as deblocking the side chain, see method (a).

In another aspect of the invention there is provided a pharmaceutical composition or preparation comprising a compound of formula (1), wherein X, R, $R^2$, $R^3$, $R^4$, $R^5$ and $R^6$ are hereinbefore defined, when $R^6$ is alkyl group it has from 1 to 8 carbon atoms and in all other cases when the substitutents have an alkyl moiety it has from 1 to 4 carbon atoms; or a pharmaceutically acceptable salt thereof; together with a pharmaceutically acceptable carrier therefor. In a particular aspect the pharmaceutical composition comprises a compound of formula (I) in effective unit dosage form.

As used herein the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops etc., depending on whether the preparation is used to treat internal or external viral infections.

For internal infections the compositions are administered orally or parenterally at dose levels, calculated as the free base, of about 0.1 to 250 mg per kg, preferably 1.0 to 50 mg per kg, of mammal body weight, and are used in man in a unit dosage form, administered eg a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavouring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10% more preferably 0.1 to 7%, most preferably 0.2% w/v. The solution may contain antioxidants, buffers, etc.

Alternatively for infections of the eye, or other external tissues e.g. mouth and skin the compositions are preferably applied to the infected part of the body of the patient as a topical ointment or cream. The compounds may be presented in an ointment, for instance with a water soluble ointment base, or in a cream, for instance with an oil in water cream base, in a concentration of from about 0.1 to 10%, preferably 0.1 to 7%, most preferably 1% w/v.

Of the compounds of formula (I), 9-(2-hydroxyethoxymethyl)guanine ($R^1=OH$, $R^2=NH_2$), 2-amino-9-(2-hydroxyethoxymethyl)adenine ($R^1=R^2=NH_2$) and their esters are most preferred, particularly because of their extremely high antiviral activity against herpes viruses. Additionally 2 amino-6-chloro-9{(2-benzoyloxyethoxy)methyl}purine, 9(2-benzoyloxyethoxymethyl)-guanine, 9-(3-hydroxypropoxymethyl)guanine, 2-amino-6-methylthio-9-(2-hydroxyethoxymethyl)purine, 9-{2-(3-carboxypropionyloxy)ethoxymethyl}guanine, 9-(2-acetoxyethoxymethyl)-2,6-diamino purine, 6-chloro-9-ethylthiomethyl purine, 9-ethylthiomethyladenine, 9-ethylthiomethyl-6-methylamino-purine also show high activity against herpes viruses and vaccinia.

In yet a further aspect of the invention there is provided a method of treating viral infections in mammals which comprises the administration of an effective non-toxic anti-viral amount, as hereinbefore defined of a substituted purine of formula (I), or a pharmaceutically acceptable salt thereof. Administration is preferably by topical application or by the oral or parenteral route.

The invention will now be illustrated with reference to the following examples.

EXAMPLE 1—6-Chloro-9-(2-benzoyloxyethoxymethyl)purine

A solution of benzonitrile (103 g) in ethylene glycol (310 g) was heated at reflux under substantially anhydrous conditions for 3 days. The reaction mixture was cooled and added to a mixture of ice and water (about 300 ml). The resulting mixture was extracted with ether ($3 \times 300$ ml) and the combined ether extract backwashed with water ($2 \times 300$ ml) and then with a saturated sodium chloride solution (300 ml). The ether solution was dried over anhydrous sodium sulfate. The ether was evaporated and the residual oil distilled to give 108 g (65% of theoretical) of ethylene glycol monobenzoate, b.p. 132°–135° C./1.5 mm Hg.

A cold (0° C.) mixture of ethylene glycol monobenzoate (166 g) and paraformaldehyde (30 g) in dry dichloroethane was saturated with dry HCl with stirring for 3 hours. The pinkish red liquid was dried over calcium chloride and the volatile components removed on a rotary evaporator at 30° C. to give 1-benzoyloxy-2-chloromethoxyethane (215 g). The Infra-Red spectrum indicated the absence of a hydroxyl group.

Following substantially the procedure of Schaeffer, et al. supra but with minor modifications, 1-benzoyloxy-2-chloromethoxyethane (4.4 g, was added with stirring to a dry solution of 6-chloropurine (3.1 g) and triethylamine (6.5 ml) in dimethylformamide (50 ml). The reaction was exothermic, immediately precipitating triethylamine hydrochloride. The reaction mixture was stirred at room temperature for 24 hours and filtered. The filtrate was evaporated on a rotary evaporator at 70° C.

The remaining thick amber oil was dissolved in the minimum amount of benzene and purified by column chromatography using a silica gel column. Benzene elution removed a trace of an unidentified material. Elution with ether first removed a small amount of ethylene glycol monobenzoate and then 6-chloro-9-(2-benzoyloxyethoxymethyl)purine. Recrystallization from ether gave a white material, m.p. 108.5°–111° C.

Example 2—9-(2-Hydroxyethoxymethyl)guanine I; ($R^1=OH$, $R^2=NH_2$)

Solid sodium nitrite (0.97 g) was added at room temperature with stirring over a period of one hour to a solution of 2-chloro-9-(2-hydroxyethoxymethyl)adenine (0.5 g) in glacial acetic acid (10 ml). The reaction mixture was stirred for an additional 4½ hours. The white solid was removed by filtration, washed with cold acetic acid and then well triturated with cold water to remove the sodium acetate present. The solid product was retained. The combined acetic acid filtrate and wash was evaporated at reduced pressure and 40° C. bath temperature and the residual oil triturated with cold water. The resulting solid material was combined with the previously isolated solid and the combined solids dried and recrystallized from ethanol to give 2-chloro-9-(2-hydroxyethoxymethyl) hypoxanthine (0.25 g), m.p. >310° C. Elemental analysis and NMR spectrum were consistent with this structure.

A mixture of 2-chloro-9-(2-hydroxyethoxymethyl) hypoxanthine (0.375 g) and methanol (80 ml) saturated with anhydrous ammonia was heated in a bomb at 125° C. for 5 hours. The bomb was cooled in an ice bath and the reaction mixture removed. Solvent and excess ammonia were removed under reduced pressure at 50° C. After the residue was triturated with cold water to remove the ammonium chloride formed, the remaining solid was dried and then recrystallized from methanol to give pure 9-(2-hydroxyethoxymethyl)guanine (0.24 g), m.p. 256.5°–257° C.

EXAMPLE 3—9-(2-Hydroxyethoxymethyl)guanine (I; $R^1=OH$, $R^2=NH_2$)

A mixture of guanine (2.0 g), ammonium sulfate (1.5 g), and hexamethyldisilazane (126 g) was heated at reflux under nitrogen overnight. Excess hexamethyldisilazane was removed by distillation at reduced pressure. Dry benzene (10 ml) was added to the residual oil and any remaining ammounium sulfate removed by filtration. To this solution was added triethylamine (4 ml) and a solution of 2-benzoyloxyethoxymethyl chloride (2.8 g) in dry benzene (15 ml) and the mixture heated at reflux under nitrogen overnight. The solvent was evaporated in a rotary evaporator at reduced pressure and the residue dissolved in 95% ethanol. The solution was warmed on a steam bath for ½ hour to effect hydrolysis of the silyl groups. The ethanol was then evaporated and the residual solid was thoroughly washed with water, filtered and dried. Recrystallization from methanol and then from water (residual guanine was insoluble in the hot solvents and was removed by filtration) afforded 9-(2-benzoyloxyethoxymethyl)guanine (0.58 g., 14% of theroetical), m.p. 222°–226° C. A later condensation of the tris-(trimethylsilyl) guanine with a 60% excess of 2-benzoyloxyethoxymethyl chloride gave a 32% yield of 9-(2-benzoyloxyethoxymethyl)guanine.

9-(Benzoyloxyethoxymethyl)guanine (0.58 g) and methanol (80 ml) saturated with ammonia were heated in a bomb at 80° C. for 16 hours. The reaction mixture was removed from the bomb and the solvent evaporated under reduced pressure. The residue was thoroughly washed with ether and then recrystallized from methanol to give 9-(2-hydroxyethoxymethyl)guanine (0.31 g., 75% of theoretical), m.p. 256.5°-257° C.

EXAMPLE 4—9-(2-Hydroxyethoxymethyl)guanine (I; $R^1=OH$, $R^2=NH_2$)

To a solution of 2-amino-9-(2-hydroxyethoxymethyl) adenine (0.22 g) in water (30 ml) was added a suspension of adenosine deaminase in aqueous ammonium sulfate (0.44 ml, containing 4.4 mg of the enzyme). The reaction mixture, which initially had a pH of 7.0, was heated at 37° C. for 18 hours, at which time the pH was 8.5 and TLC (silica gel plates developed in 15% methanol-85% chloroform) indicated a single product different from starting material. The reaction mixture was thoroughly chilled in an ice bath and the resulting white solid removed by filtration and thoroughly washed with cold water. The product was dried at 100° C./0.1 mm Hg for 16 hours to give 0.20 g of 9-(2-hydroxyethoxymethyl)-guanine. $\frac{1}{4}$ $H_2O$, the structure of which was confirmed by m.p., TLC, U.V., NMR and mass spectroscopy analysis. Recrystallization from methanol gave the anhydrous 9-(2-hydroxyethoxymethyl)guanine.

EXAMPLE 5—Properties of 9-(2-hydroxyethoxymethyl)guanine)

9-(2-Hydroxyethoxymethyl)guanine was determined by U.V. to be soluble in either water or 0.1 N aqueous hydrochloric acid to the extent of about 0.2%. It was stable in either 0.01 N or 0.1 N aqueous hydrochloric acid at 26° C. and at 37° C., showing no indication of hydrolysis after one week. However, in 1 N aqueous hydrochloric acid at either 26° C. or 37° C., it slowly hydrolyzed to guanine within one week.

EXAMPLE 6—9-(2-Hydroxyethoxymethyl)guanine

2-Mercaptoethanol (0.75 ml) dissolved in 1 M methanolic sodium methylate (7.5 ml) was added to 2-amino-6-chloro-9-(2-benzoyloxyethoxymethyl)purine (0.89 g) in methanol (150 ml). The reaction mixture was heated at reflux for 3 hours under nitrogen. The solvent was evaporated under reduced pressure and the residue dissolved in water. The aqueous solution was heated on a steam bath for 2 hours, chilled, and acidified to pH 5.0 with acetic acid. The resulting white solid was removed by filtration, washed well with ice cold water and ether, and then recrystallized from methanol to give a 45% yield of 9-(2-hydroxymethoxymethyl)guanine.

EXAMPLE 7—9-(2-(3-Carboxypropionyloxy)ethoxymethyl)guanine

A mixture of 9-(2-hydroxyethoxymethyl)guanine (0.25 g), succinic anhydride (0.55 g) and pyridine (50 ml) was heated under anhydrous conditions on a steam bath overnight. The solvent was evaporated under reduced pressure at <40° C., the last trace being removed azeotropically with toluene. The residue was triturated with acetone and the product removed by filtration. Recrystallization from methanol afforded 9-(2-(3-carboxypropionyloxy)ethoxymethyl) guanine, m.p. 203°-207° C. (sinter 190° C.), in 44% yield.

EXAMPLE 8—9-(3-Hydroxypropoxymethyl)guanine

Sodium benzoate (96.32 g) in DMF (690 ml) was heated to 80° C., and 1-chloro-3-hydroxypropane (63.06 g) was added over 15 minutes. The temperature increased to 135° C., and the reaction mixture was heated at 135°-175° C. for 3 hours. Filtration removed 38 g of sodium chloride (97% of theory). The filtration was partially evaporated at reduced pressure at <40° C. The concentrated filtrate was poured into ice water and extracted well with ether. The combined ether extracts were washed with water, dried over anhydrous sodium sulfate, and evaporated. The residual oil was distilled through a Vigreux column to give 3-benzoyloxy-1-propanol (85.2 g), b.p. 124°-132° C. at 0.055 mm Hg.

Anhydrous hydrogen chloride was bubbled into a solution of 3-benzoyloxy-1-propanol (15.02 g) and paraformaldehyde (2.49 g) in dichloromethane (35 ml) for 1 hour at 0° C. The solvent was evaporated under reduced pressure at <40° C. giving a 92% yield of crude 3-benzoyloxypropoxymethyl chloride which was used without purification.

A solution of trimethylsilylated guanine in benzene (25 ml) prepared as in Example 6 (from 2.0 g of guanine) containing triethylamine was heated at reflux and 3-benzoyloxypropoxymethyl chloride (2.96 g) dissolved in benzene (15 ml) was added over a 3 hour period. The reaction mixture was heated at reflux under nitrogen overnight. The solvent was removed under reduced pressure, and 95% ethanol and methanol were added to the residual oil. The mixture was heated on a steam bath for several minutes and the solvent then evaporated under reduced pressure. Chloroform (200 ml) was added and the resulting solid removed by filtration. The solid was dissolved in a minimal amount of DMF, filtered (to remove any guanine present) and reprecipitated by the addition of water. Recrystallization from methanol (with charcoaling) gave 9-(3-benzoyloxypropoxymethyl)guanine (0.94 g) as a pale yellow solid, m.p. 198°-201° C.

A mixture of 9-(3-benzoyloxypropoxymethyl)guanine (0.5 g) and aqueous 45% methylamine (10 ml) was stirred overnight at room temperature. Excess methylamine and water was evaporated at <30° C. under reduced pressure and the residue recrystallized from ethanol to give 9-(3-hydroxypropoxymethyl)guanine (0.24 g), m.p. 223° C. (with resolidification), as the $\frac{1}{2}$ hydrate.

EXAMPLE 9

| Oil in Water Cream base | |
| --- | --- |
| 9-(2-hydroxyethoxymethyl)guanine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 10

| Water Soluble Ointment Base | |
| --- | --- |
| 2-amino-9-(2-hydroxyethoxymethyl)adenine | 0.5 g |
| Glycerol | 15.0 g |
| Macrogol 300 | 20.0 g |
| Polyethylene Glycol 1500 | 64.5 g |

EXAMPLE 11

| Tablet - (Total weight 359 mg) | |
| --- | --- |
| 9-(2-hydroxyethoxymethyl)guanine | 100 mg |
| Lactose | 200 mg |
| Starch | 50 mg |
| Polyvinylpyrrolidone | 5 mg |
| Magnesium Stearate | 4 mg |

EXAMPLE 12

A solution of 9-(2-hydroxyethoxymethyl)guanine (4.73 g) in 97% formic acid (24 ml) was stirred at room temperature overnight. The amber solution was diluted with about 200 ml of dry ether and chilled. The resulting white precipitate was filtered, dried and recrystallized from dry dimethylformamide to give 9-(2-formyloxyethoxymethyl)guanine (3.6 g, m.p. 225°–227° C.).

EXAMPLE 13

| Tablet - (Total weight 359 mg) | |
| --- | --- |
| 9-(2-Formyloxyethoxymethyl)guanine | 100mg |
| Lactose | 200mg |
| Starch | 50mg |
| Polyvinylpyrrolidone | 5mg |
| Magnesium stearate | 4mg |

EXAMPLE 14

The following compounds are also preferred:

| Compound | m.p. |
| --- | --- |
| 9-[2-(p-Fluorosulfonylbenzamido)ethoxymethyl]adenine | 201–202° C. |
| 9-(2-Bromoacetamidoethoxymethyl)adenine hydrogen oxalate | 132–133° C. |
| 9-[1-(2-Hydroxyethoxy)octyl]adenine | 121–123° C. |
| 6-Dimethylamino-9-[1-(2-hydroxyethoxy)ethyl]purine | 86–88° C. |
| 9-(2-Amino-1-methylethoxy)methyladenine dihydrochloride | 181–182° C. (eff) |
| 9-(2-Hydroxyethoxymethyl)-6-mercaptopurine | decomposes |
| 9-(2-Hydroxypropoxy)methyladenine | 164–167° C. |
| 9-(1,3-dibenzyloxy-2-propoxymethyl)adenine | 120.5–122.5° C. |
| 9-(2-Sulfamoyloxyethoxymethyl)adenine. | 172–173.5° C. |
| 9-(2-N-Carbobenzoxyphenylalanylamidoethoxymethyl)adenine | 208–210° C. |
| 9-(1,3-Dibenzyloxy-2-propoxymethyl)-6-mercaptopurine monohydrate | 162–164° C. |
| 9-(3-Benzoylpropoxymethyl)guanine | 198–201° C. |
| 9-(2-Benzoyloxyethoxymethyl)purine | 128–130° C. |
| 9-[1-(2-Hydroxyethoxy)ethyl]guanine | >260° C. |
| 9-Ethoxymethylguanine | 275–280° C. (dec.) |
| 9-[(2-Amino-1-cyclopentylethoxy)methyl]-6-dimethylaminopurine dihydrochloride | 153–154° C. (dec.) |
| 9-[(2-Amino-1-methylethoxy)methyl]-6-dimethylaminopurine hydrochloride | 201–203° C. |
| 9-[(2-N-Carbobenzoxyphenylalanylamido-1-cyclopentylethoxy)methyl]-6-dimethylaminopurine | 146–147° C. |
| 6-Diethylamino-9-[1-(2-benzoyloxyethoxy)ethyl]purine | 83–86° C. |
| 2-Amino-6-dimethylamino-9-[1-(2-hydroxyethoxy)ethyl]purine hemihydrate | 92–94° C. |
| 2-Amino-6-chloro-9-[1-(2-benzoyloxyethoxy)ethyl]purine | 125–130° C. |
| 9-[(2-N-Carbobenzoxyphenylalanylamido-1-methylethoxy)methyl]-6-dimethylaminopurine | 149–152° C. |
| 2-Amino-9-(2-benzoyloxyethoxymethyl)purine | 149–154° C. |
| 9-(2-Benzoyloxyethoxymethyl)-2,6-diazidopurine | 124.5–125.0° C. |
| 9-Carboxymethoxymethyl-2,6-diaminopurine . 0.02 2-methoxyethanol | ~250° C. (dec.) |
| 9-(4-Hydroxy-n-butoxymethyl)guanine hemihydrate | 234° C. with resolidification and decomposition |
| 6-Dimethylamino-9-(2-hydroxypropoxy)-methylpurine hydrochloride | 144–146° C. |
| 9-[(2-Phenylalanylamido-1-methylethoxy)methyl]-6-dimethylaminopurine one quarter hydrate | 77–80° C. |
| 9-[(2-Phenylalanylamido-1-phenylethoxy)methyl]-6-dimethylaminopurine one quarter hydrate | sinter ~135° C. melt 142–144° C. |
| 2-Acetamido-9-(2-acetyloxyethoxymethyl)hypoxanthine | 202.5–204.5° C. |

The above compounds were prepared by the methods disclosed herein.

EXAMPLE 15—Treatment of Herpes Simplex

Both eyes of a New Zealand White rabbit were infected with a suspension of the PH8 strain of type I herpes simplex virus using the teaching of the method of Jones, B. J. Wise, J. B. and Patterson A. entitled *The measurement of enhancement or inhibition of virus replication in the cornea. Evaluation of drug effects in the eye*, 83–97. Symposium of the Royal Society of Medical, ed. Pigott, P. V., Association of Medical Advisers to the Pharmaceutical Industry, London, 1968.

One of the infected eyes of the rabbit was then treated topically beginning on the 4th day after infection with two drops of a 1% aqueous solution of 2-amino-9-(2-hydroxyethoxymethyl) adenine for a period of four days 5 times per day. On the fifth day after treatment began the treated infected eye was free of infection whereas the non-treated eye continued to exhibit the infection.

Example 16—Treatment of Herpex Simplex

The method of Example 15 was followed except that a 1% aqueous solution of 9-(2-hydroxymethyl) guanine was administered beginning on the 3rd day after infection. The results were the same as in Example 15.

Example 17—9-(2-Hydroxyethoxymethyl)guanine

A solution of 44 mg of 9-(2-hydroxyethoxymethyl)-2-methylthiohypoxanthine in 50 ml of $NH_3$ saturated EtOH was heated in a stainless steel vessel at 140° for 60 hr. The reaction solution was spin evaporated in vacuo and the residual solid was recrystallized from EtOH; yield, 15 mg. (39%). The tlc, UV, NMR, and mass spectral data were the same as that for authentic 9-(2-hydroxyethoxymethyl)guanine prepared in Example 5.

Example 18—9-(2-acetzloxyethoxymethyl)guanine

A mixture of 9-(2-hydroxyethoxymethyl)guanine (4.6 g), dry dimethylformamide (46 ml), acetic anhydride (16 ml) and dry pyridine (24 ml) was stirred at room temperature overnight. The resulting white solid was removed by filtration and dissolved in warm dimethylformamide (100 ml), pyridine (10 ml) and acetic anhydride (8 ml) added and the mixture stirred for 18 hr. The white solid formed was removed by filtration, washed with ethyl acetate and recrystallized from dimethylformamide to give 9-(2-acetyloxyethoxymethyl)guanine (3.3 g), m.p. 240°–241° C.

Example 19—9-(2-Propionyloxyethoxymethyl)guanine

A mixture of 9-(2-hydroxyethoxymethyl)guanine (1.0 g) and dry dimethylformamide (50 ml) was heated on a steam bath until most of the solid had dissolved. It was then cooled to room temperature. Dry pyridine (10 ml) and propionic anhydride (2.9 ml) was added and the mixture stirred at room temperature overnight. Additional propionic anhydride (1.0 ml) was added and the mixture stirred for an additional 18 hr. The reaction mixture was diluted with ethyl acetate, chilled and the resulting solid removed by filtration. This was recrystallized from dimethylformamide to give 9-(2-propionyloxyethoxymethyl)guanine (0.9 g), m.p. 223°–226° C.

Example 20—9-[2-(2,2-Dimethylpropionyloxy)ethoxymethyl]-guanine

A mixture of 9-(2-hydroxyethoxymethyl)guanine (2.46 g), dry pyridine (400 ml), and pivalic anhydride (6.5 ml) was heated on a steam bath for a total of 33 days. On day 11 additional pyridine (150 ml) was added, and on day 27 dimethylformamide (50 ml) was added. Volatiles were removed under reduced pressure, and the residue was triturated with ethyl acetate. The insoluble solid was removed by filtration and dissolved in methanol-acetone. Silica gel (3 g) was added and the solvent evaporated. The residue was added to a column of silica gel (180 g) in acetone. Elution with acetone yielded an initial fraction of N,O-diacylated material followed by a fraction containing the desired monoacylated product. The acetone was evaporated from this latter fraction, and the residue was recrystallized from dimethylformamide-acetonitrileethyl acetate to give 9-[2-(2,2-dimethylpropionyloxy)ethoxymethyl]guanine (0.5 g), m.p. 245°–246° C.

Example 21—9-(2-aminoethoxymethyl)guanine

A dispersion of N-(2-hydroxyethyl)phthalimide (19.1 g) and paraformaldehyde (3.0 g) in 1,2-dichloroethane (250 ml) was cooled in an ice-salt-acetone bath and saturated with dry hydrochloric acid with stirring. After 4 hours the mixture was dried over calcium chloride, filtered and evaporated under reduced pressure to give N-(2-chloromethoxyethyl)phthalimide (21.9), m.p. 69°–72° C.

To a stirred solution of tris trimethylsilylguanine (16.5 g) in toluene (50 ml) was added N-(2-chloromethoxyethyl)phthalimide (17.0 g) and triethylamine (23 ml). The reaction mixture was heated at reflux under nitrogen for 29 hours, cooled and evaporated under reduced pressure giving a dark brown oil. The oil was digested in ethanol (400 ml) on a steam bath for 40 minutes, giving a solid which was collected and washed with ethanol and ether. It was recrystallized from 2-methoxyethanol to give 9-(2-phthalimidoethoxymethyl)guanine hydrate (14.4 g), m.p. >240° C. (dec.). A mixture of 9-(2-phthalimidoethoxymethyl)guanine hydrate (0.94 g), hydrazine (2 ml) and ethanol (100 ml) was heated at reflux with stirring for one hour. The reaction mixture was filtered hot, and the filtrate was cooled and evaporated under reduced pressure. Ethanol was added and the mixture re-evaporated. This was repeated three times. The residual solid was stirred with 3% aqueous acetic acid (50 ml) for 30 minutes and filtered. The solids were washed with water (15 ml), and the wash and filtrate combined. The combined wash and filtrate was evaporated under reduced pressure at <35° C. to a small volume, diluted with ethanol and evaporated to dryness. The pasty, white solid was dispersed in a small amount of ethanol and diluted with a few ml ether to give a granular solid which was collected, washed with ethanol and dried. Recrystallization from ethanol-water gave 9-(2-aminoethoxymethyl)guanine acetate monohydrate (0.43 g), m.p. (~135° C. melts and resolidifies) 174°–176° C.

Example 22—9-(2-hydroxyethoxymethyl)guanine

To a mixture of acetic anhydride (1.2 ml) and p-toluenesulfonic acid (0.09 g) was added with stirring dioxolane (1.02 g)—caution, exothermic. The solution was allowed to cool for several minutes. Diacetylguanine (1.45 g) and dry toluene (9 ml) were added and the reaction mixture was stirred at reflux for 18 hr. and then allowed to cool to room temperature. The toluene was decanted off and the residue triturated several times with benzene. Methanol (10 ml) was added to the residue and evaporated under reduced pressure. To the residue was added 40% aqueous methylamine (10 ml) and the mixture heated on a steam bath for 20 min. The water and methylamine were removed under reduced pressure, ethanol (10 ml) was added and evaporated. The residue was thoroughly extracted with boiling methanol (700 ml total) and the combined extracts evaporated. The resulting solid was triturated with cold ethanol and then recrystallized from methanol to give 9-(2-hydroxyethoxymethyl)guanine (0.3 g).

EXAMPLE 23—9-(2-hydroxyethoxymethyl)guanine Monophosphate

Phosphorous oxychloride (0.03 ml) was added in one portion to a stirred suspension of 2-chloro-9-(2-hydroxyethoxymethyl)hypoxanthine (20 mg) in triethyl phosphate (0.3 ml) at −8° C. The temperature was allowed to rise to 0° C. over 30 min. The reaction mixture was then stirred at 0° C. for 40 min and at +5° C. for 50 min. It was then poured onto ice, and the pH was adjusted to 7 with 2 N potassium hydroxide. The resulting solution was extracted twice with chloroform (2×2 ml). The aqueous phase was adjusted to pH 8–8.5 with 2 N potassium hydroxide, and barium acetate (105 mg) was added. The resulting barium phosphate precipitate was removed by filtration. The supernatant was treated with a large excess of ethanol, precipitating crude barium 2-chloro-9-(2-hydroxyethoxymethyl)hypoxanthine monophosphate. The solid was collected by filtration and suspended in ethanol. The ethanolic suspension was then heated on a steam bath for several minutes, cooled and filtered. The collected precipitate was washed with anhydrous ether and dried, giving barium 2-chloro-9-(2-hydroxyethoxymethyl)hypoxanthine monophosphate (26 mg).

Ammonium sulfate (3.96 mg) was added to a stirred suspension of barium 2-chloro-9-(2-hydroxyethoxymethyl)hypoxanthine monophosphate (7 mg) in water (0.5 ml). The mixture was stirred at ambient temperature for 15 min and then cooled in an ice bath. The precipitated barium sulfate was removed by filtration and washed with water (1 ml) and ethanol (10 ml). The combined filtrate and washings were evaporated under reduced pressure, and the resulting residue dissolved in methanol (3 ml). The methanolic solution was transferred to a Teflon ® lined stainless steel bomb, and methanol (8 ml) saturated with gaseous ammonia at ice bath temperature was also added to the bomb. The sealed bomb was placed in a 122° C. oven for 4 hr., chilled and opened. Solvent was evaporated to minimal volume. The residual reaction mixture was spotted on Eastman Chromatogram ® cellulose TLC sheets which were then developed in n-propanol:water (70:30 v/v). The bands at Rf $_{0.16}$ and 0.34 were excised, suspended in Tris buffer (0.6 ml) at pH 8, and the cellulose was removed by filtration.

These bands were shown to contain 9-(2-hydroxyethoxymethyl)guanine monophosphate and 2-chloro-9-(2-hydroxyethoxymethyl)hypoxanthine monophosphate by enzymatic dephosphorylation with alkaline phosphatase to 9-(2-hydroxyethoxymethyl)guanine and 2-chloro-9-(2-hydroxyethoxymethyl)hypoxanthine, respectively. Alkaline phosphatase (2 μl) from *E. coli* was added to the filtrate and the mixture was heated at 32° C. for 2 hr. It was then examined by thin layer chromatography on Eastman Chromatogram ® cellulose sheets in three solvent systems:

(a) n-propanol:water (70:30 v/v)
(b) water
(c) n-propanol:conc. ammonium hydroxide:water (60:30:10 v/v)

Two spots were present in each system, corresponding to 9-(2-hydroxyethoxymethyl)guanine (A) and 2-chloro-9-(2-hydroxyethoxymethyl)hypoxanthine (B).

| Solvent System | Rf (A) | Rf (B) | Rf of Reaction Product |
|---|---|---|---|
| (a) | 0.51 | 0.64 | 0.51 and 0.65 |
| (b) | 0.68 | 0.97 | 0.67 and 0.97 |
| (c) | 0.51 | 0.71 | 0.50 and 0.71 |

Pharmaceutically acceptable salts of 9-(2-hydroxyethoxymethyl)guanine monophosphate are prepared by neutralizing the monophosphate in its acidic form with an equivalent (i.e. equinormal) amount of a base, e.g. hydroxide, bicarbonate, carbonate, containing the desired cation, e.g. sodium, potassium, ammonium, calcium. They may also be prepared by exchange reactions. For example, the slightly soluble barium salt of 9-(2-hydroxyethoxymethyl)guanine monophosphate is treated in aqueous suspension with sodium sulfate to remove the barium as the very insoluble barium sulfate, leaving sodium 9-(2-hydroxyethoxymethyl)guanine monophosphate in solution.

Example 24—9-(2-Hydroxyethoxymethyl)guanine Monophosphate

Phosphorous oxychloride (0.76 ml) was added to a stirred, cooled (−10° C.) mixture of 9-(2-hydroxyethoxymethyl)guanine (0.225 g) and triethyl phosphate (5 ml). The temperature of the reaction mixture was allowed to rise to 0° C. over 30 min. and was held at this temperature for 2 hr. It was then poured onto a mixture of ice and water, and the pH was adjusted to 7 with 2 N potassium hydroxide. The resulting solution was extracted twice with chloroform and once with ether. The pH of the remaining aqueous solution was adjusted to 7.1 with 2 N potassium hydroxide and was then lyophlized. The resulting white solid was dissolved in water (7 ml), and methanol (7 ml) was added to precipitate the inorganic salts which were then removed by filtration. Acetone (70 ml) was added to the filtrate, precipitating a white gum. The gum was dissolved in water (7 ml), ethanol (7 ml) added and the mixture filtered. A large excess of acetone (70 ml) was added, again precipitating the gum. The gum was dissolved in ethanol (ca. 20 ml) and the solvent was removed by flash evaporation, giving a white powder (2.6 g) which was a mixture of inorganic salts and the desired phosphate. The solid was dissolved in water (10 ml) applied to a Bio-Gel P-2 column (200–400 mesh, 2.7×90 cm) and eluted with water. The majority of the monophosphate was eluted in a 50 ml volume after 166 ml of eluate had been collected, as shown by thin layer chromatography on Eastman Chromagram ® cellulose in n-propanol:water (70:30 v/v); Rf=0.26 for 9-(2-hydroxyethoxymethyl)guanine phosphate and Rf=0.11 for potassium 9-(2-hydroxyethoxymethyl)guanine phosphate. The eluate was lyophilized to give 0.82 g of a solid which was shown by ultraviolet spectroscopy to contain 0.2 g of monophosphate product. The solid was dissolved in water (30 ml) and the pH of the solution was adjusted to 6 with 6 N hydrochloric acid. The product was adsorbed onto 14 ml of packed charcoal (Fischer 5-690B, 50–200 mesh, acid washed and deactivated with toluene). The charcoal was washed well with water and eluted with 70 ml of 50% aqueous ethanol containing 2% concentrated ammonium hydroxide. The solvent was evaporated under reduced pressure to give ammonium 9-(2-hydroxyethoxymethyl)guanine monophosphate (0.048 g); Rf=0.30 on Eastman cellulose in n-propanol:water (70:30 v/v).

Example 25—Tablet

| | |
|---|---|
| Sodium 9-(2-hydroxyethoxymethyl)guanine phosphate | 100 mg |
| Lactose | 200 mg |
| Starch | 50 mg |
| Polyvinylpyrrolidone | 5 mg |
| Magnesium stearate | 4 mg |
| Total weight | 359 mg |

I claim:

1. 9-(2-hydroxyethoxymethyl) guanine monophosphate or a pharmaceutically acceptable salt thereof.

2. 9-(2-hydroxethoxymethyl) guanine monophosphate.

3. A compound of the formula

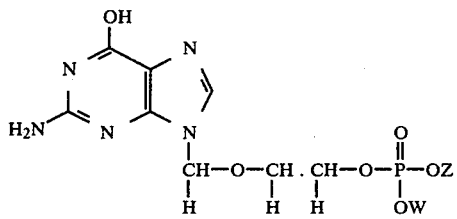

where Z is a pharmaceutically acceptable cation and W is H or a a pharmaceutically acceptable cation.

4. The compound of claim 3 where Z is sodium, potassium, or ammonium and W is H.

5. The compound of claim 3 where Z is sodium and W is H.

6. The compound of claim 3 where Z is ammonium and W is H.

7. A pharmaceutical composition comprising an effective non-toxic antiviral amount of 9-(2-hydroxyethoxymethyl) guanine monophosphate or a pharmaceutically acceptable salt thereof and a pharmaceutically acceptable carrier.

8. A pharmaceutical composition comprising an effective non-toxic antiviral amount of 9-(2-hydroxyethoxymethyl) guanine monophosphate and a pharmaceutically acceptable carrier therefore.

9. A pharmaceutical composition comprising an effective nontoxic antiviral amount of a compound of the formula

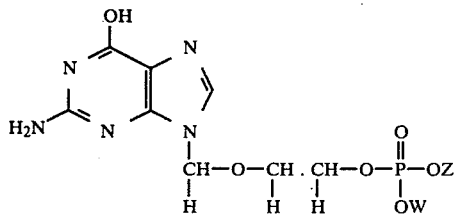

where Z is a pharmaceutically acceptable cation, and W is H or a pharmaceutically acceptable cation and a pharmaceutically acceptable carrier.

10. The composition of claim 9 where Z is sodium, potassium, or ammonium and W is H.

11. The composition of claim 9 where Z is sodium and W is H.

12. The composition of claim 9 where Z is ammonium and W is H.

13. The composition of claim 7 in unit dosage form for parenteral or oral administration.

14. The composition of claim 13 in the form of a tablet or capsule.

15. The composition of claim 7 in which the amount is 1 to 250 mg. calculated as the free phosphate.

16. The method of treating a susceptible viral infection in a mammal which comprises the administration to said mammal of an effective, antiviral, non-toxic amount of 9-(2-hydroxyethoxymethyl)guanine monophosphate or a pharmaceutically acceptable salt thereof.

17. The method of claim 16 in which the amount is 0.1 to 250 mg/kg calculated as free base of mammal body-weight.

18. The method of claim 16 in which the compound is orally, parenterally or topically administered.

19. The method of claim 16 in which the virus causing said infection is a herpes simplex virus.

20. The method of claim 16 in which the virus is *herpes zoster.*

21. The method of claim 16 in which the virus is *herpes varicella.*

22. The method of treating *herpes simplex* or *herpes zoster* infection in mammals which comprises orally administering to said mammals in unit dosage form 0.1 to 250 mg/kg calculated as base of the 9-(2-hydroxyethoxymethyl)quanine monophosphate or a pharmaceutically acceptable salt thereof.

23. The method of claim 22 in which 9-(2-hydroxyethoxymethyl)quanine monophosphate is administered.

24. The method of claim 22 in which a pharmaceutically acceptable salt of 9-(2-hydroxyethoxymethyl)guanine monophosphate is administered.

25. The method of claim 22 in which the compound is administered as part of a tablet.

26. The method of claim 23 in which the compound is administered as part of a tablet.

27. The method of claim 24 in which the compound is administered as part of a tablet.

28. The compound of claim 3 wherein W is hydrogen.

29. The composition of claim 9 wherein W is hydrogen.

30. The composition of claim 8 in unit dosage form for parenteral or oral administration.

31. The composition of claim 9 in unit dosage form for parenteral or oral administration.

32. The composition of claim 8 in which the amount is 1 to 250 mg. calculated as the free phosphate.

33. The composition of claim 9 in which the amount is 1 to 250 mg. calculated as the free phosphate.

34. The method of claim 16 in which 9-(2-hydroxyethoxymethyl)guanine monophosphate is administered.

35. The method of treating a susceptable viral infection in a mammal which comprises the administration to said mammal of a compound of the formula

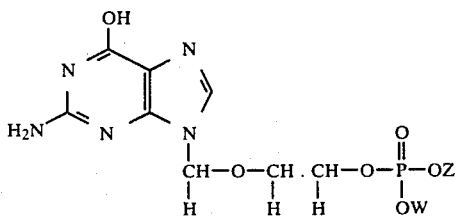

where Z is a pharmaceutically acceptable cation and W is H or a pharmaceutically acceptable cation.

36. The method of claim 35 where Z is sodium potassium or ammonium and W is H.

37. The method of claim 35 where Z is sodium and W is H.

38. The method of claim 35 where Z is ammonium and W is H.

39. The method of treating a cytomegalovirus infection in a mammal which comprises administering an effective cytomegalovirus infection treatment amount of 9-(2-hydroxyethoxymethyl)guanine monophosphate or a pharmaceutically acceptable salt thereof to the infected mammal.

40. The method of treating an adenovirus infection in a mammal which comprises administering an effective adenovirus infection treatment amount of 9-(2-hydroxyethoxymethyl) guanine monophosphate or a pharmaceutically acceptable salt thereof to the infected mammal.

41. The method of claim 40 in which the adenovirus is adenovirus 5.

42. The method of treating a rhino virus infection in a mammal which comprises administering an effective rhino virus infection treatment amount of 9-(2-hydroxyethoxymethyl) guanine monophosphate or a pharmaceutically acceptable salt thereof to the infected mammal.

43. The method of treating a Mengo virus infection in a mammal which comprises administering an effective Mengo virus infection treatment amount of 9-(2-hydroxyethoxymethyl) guanine monophosphate or a pharmaceutically acceptable salt thereof to the infected mammal.

44. The method of treating a Sindbis virus infection in a mammal which comprises administering an effective Sindbis virus infection treatment amount of 9-(2-hydroxyethoxymethyl) guanine monophosphate or a pharmaceutically acceptable salt thereof to the infected mammal.

45. The method of treating a vaccinia virus infection in a mammal which comprises administering an effective vaccinia virus infection treatment ammount of 9-(2-hydroxyethoxymethyl) guanine monophosphate or a pharmaceutically acceptable salt thereof to the infected mammal.

46. The method of treating a varicella virus infection in a mammal which comprises administering an effective varicella virus infection treatment amount of 9-(2-hydroxyethoxymethyl) guanine monophosphate or a pharmaceutically acceptable salt thereof to the infected mammal.

47. The method of treating a *herpes simplex* virus infection in a mammal which comprises administering an effective *herpes simplex* virus infection treatment amount of 9-(2-hydroxyethoxymethyl) guanine monophosphate or a pharmaceutically acceptable salt thereof to the infected mammal.

48. The method of treating a *herpes zoster* virus infection in a mammal which comprises administering an effective *herpes zoster* virus infection treatment amount of 9-(2-hydroxyethoxymethyl) guanine monophosphate or a pharmaceutically acceptable salt thereof to the infected mammal.

49. A pharmaceutical composition suitable for administration to the eye to treat a virus infection thereof which comprises an effective virus treatment amount of the compound 9-(2-hydroxyethoxymethyl) guanine monophosphate or a pharmaceutically acceptable salt thereof and a pharmaceutically acceptable carrier therefor.

50. The composition of claim 49 in the form of an ointment.

51. The composition of claim 49 in the form of a cream.

52. The composition of claim 49 in the form of eye drops.

53. The composition of anyone of claims 49 to 52 in which the concentration of the compound or pharmaceutically acceptable salt thereof is 0.1 to 10%.

* * * * *

UNITED STATES PATENT AND TRADEMARK OFFICE
CERTIFICATE OF CORRECTION

PATENT NO. : 4,287,188
DATED : September 1, 1981
INVENTOR(S) : Howard J. Schaeffer It is certified that error appears in the above-identified patent and that said Letters Patent is hereby corrected as shown below:

In the claims:

Col. 19, (Claim 8), line 44 - correct "therefore" to
-- therefor --;

Col. 20 (Claim 22), line 26 -- correct "quanine" to --guanine--;

Col. 20 (Claim 23), line 29 - correct "quanine" to -- guanine --'

Col. 21 (Claim 36), line 1 - after "sodium" insert --,--;

Col. 22 (Claim 53), line 1 - correct "anyone" to -- any one --.

Signed and Sealed this

Fifth Day of February 1985

[SEAL]

Attest:

DONALD J. QUIGG

Attesting Officer     Acting Commissioner of Patents and Trademarks